United States Patent [19]

Mathis et al.

[11] Patent Number: 4,927,923
[45] Date of Patent: May 22, 1990

[54] MACROPOLYCYCLIC RARE EARTH COMPLEXES AND APPLICATION AS FLUORESCENT TRACERS

[75] Inventors: Gérard Mathis, Bagnols S/Ceze; Jean-Marie Lehn, Strasbourg, both of France

[73] Assignee: Compagnie Oris Industries, Gif-Sur-Yvette, France

[21] Appl. No.: 778,215

[22] Filed: Sep. 20, 1985

[30] Foreign Application Priority Data

Sep. 26, 1984 [FR] France ................................ 84 14799

[51] Int. Cl.$^5$ ........................................... G01N 00/00
[52] U.S. Cl. .................................... 540/456; 540/469; 540/472
[58] Field of Search ................ 549/352; 540/456, 469, 540/472

[56] References Cited

U.S. PATENT DOCUMENTS

| | | | |
|---|---|---|---|
| 3,847,949 | 11/1974 | Pedersen et al. | 540/456 |
| 3,888,877 | 6/1975 | Lehn | 260/327 |
| 3,966,766 | 6/1976 | Lehn | 260/327 |
| 4,058,732 | 11/1977 | Wieder | 250/461 |
| 4,156,683 | 5/1979 | Lehn | 260/338 |
| 4,374,120 | 2/1983 | Soini et al. | 424/7 |
| 4,631,119 | 12/1986 | Gokel | 549/352 X |
| 4,659,815 | 4/1987 | Pacey et al. | 436/74 |
| 4,734,376 | 3/1988 | Pacey et al. | 436/164 |

FOREIGN PATENT DOCUMENTS

| | | | |
|---|---|---|---|
| 68875 | 1/1983 | European Pat. Off. | 101/12 |
| 85320 | 1/1983 | European Pat. Off. | 498/8 |
| 223613 | 5/1987 | European Pat. Off. | 540/456 |
| 3033691 | 3/1981 | Fed. Rep. of Germany | 103/50 |
| 2088519 | 1/1972 | France . | |

OTHER PUBLICATIONS

E. Buhleier et al.; 2,2'-Bipyridin als Baustein fur neue AxaKronenther udn Cryptanden; Chem. Ber. 1111, 200-204, (1978).

Joseph P. Konopelski et al.; Synthesis, Cation Binding, and Photophysical Properties of Macrobicyclic Anethracenocryptands; J. Chem. Soc., Chem. Commun., 1985, pp. 433-436.

Juan-Carlos Rodriguez et al.; Synthesis of the Sodium Cryptates of Macrobicyclic Ligands Containing Bipyridine and Phenanthroline Groups; Helvetica Chimica Acta, vol. 67, (1984), pp. 2264-2269.

"Fluorescence and Laser Action in Rare Earth Chelates", A. P. B. Sinha, Spectroscop. Inorg. Chem. 2, 1971, pp. 255-288.

"Synthesis and X-ray Structre of N[CH$_2$)$_2$O(2,6-C$_6$H$_3$-N)O(CH$_2$)$_2$]$_3$N:a D$_3$ Macrobicyclic Ligand Capped by Two sp$^2$ Nitrogen Atoms", J. Am. Chem. Soc., 1979, 101, p. 1047.

"Chirale Makrobicyclische und Makrotricyclische Liganden", Von Bernard Dietrich, Jean-Marie Lehn and Jacques Simon, Angew. Chem. 86, (1974), p. 443.

"Multisite Molecular Receptors and Co-Systems Ammonium Cryptates of Macrotricyclic Structures", F. Kotzyba-Hibert, J. M. Lehn and P. Vierling, Tetrahedron Letters, vol. 21, 1980, pp. 941-944.

"Cryptates: The Chemistry of Macropolycyclic Inclusion Complexes", Jean-Marie Lehn, Accounts of Chemical Research, vol. 11, No. 2, Feb. 1978, pp. 49-57.

"Dynamic Properties of Molecular Complexes and Receptor-Substrate Complementarity, Molecular Dynamics of Macrotricyclic Diammonium Cryptates," Jean-Pierre Kintzinger et al., Journal of the Chemical Society, Chemical Communications 1981, pp. 834-836.

"Preparation and Characterization of Some Bifunctional Lanthanide Cryptates", Otto A. Gansow et al., Chemical Abstracts, vol. 99, No. 10, Sep. 5, 1983, Ref. No. 81500g, p. 676.

Primary Examiner—Christine M. Nucker
Attorney, Agent, or Firm—Woodcock Washburn Kurtz Mackiewicz & Norris

[57] ABSTRACT

The invention relates to macropolycyclic rare earth complexes, namely cryptates which are useful as fluorescent tracers.

10 Claims, No Drawings

MACROPOLYCYCLIC RARE EARTH COMPLEXES AND APPLICATION AS FLUORESCENT TRACERS

The present invention, which is the result of work carried out in collaboration with Professor J. M. LEHN and his research team at the Université Louis Pasteur in Strasbourg, relates to the field of fluorescence and more particularly of fluorescent macropolycyclic complexes which are especially suitable as tracers in immunological determinations.

It is known that detection methods using fluorescence are intrinsically very sensitive and could make it possible to obtain lower detection limits than those reached by means of radioactivity measurements, in particular through the use of laser sources (I. Wieder, Immunofluorescence and related staining techniques, 1978, Elsevier).

In practice, however, these detection limits are not reached because the measurement is made in a matrix which does not have the properties required to achieve this optimum. In general, the measurement medium is turbid and favors diffusion, and other molecules fluorescing at the same wavelength can be present in the measurement medium.

In some cases, the improvements made to the measuring equipment are not sufficient to substantially improve this detection limit or are very expensive (laser, monochromators, etc.).

This state of things is even more troublesome in the field of biochemistry and immunology, where very small quantities of active molecules have to be measured in biological media which can be turbid or can contain proteins or other molecules which are themselves fluorescent (turbidity and intrinsic fluorescence of the serum).

In immunological determinations using a fluorescent tracer, when the antigen or antibody is labeled with the fluorescent molecule, the latter must possess the following properties:

it must possess a chemical function which permits coupling with the biological molecule without denaturing it or modifying its immunological properties;

the molar absorption coefficient of the fluorescent molecule must be as high as possible;

the quantum yield of fluorescence must be the highest;

the Stokes shift must be as large as possible;

the emission wavelength must be greater than 500 nm if possible; and it must be soluble in water or buffer solutions.

These conditions are specified for example in the article by E. SOINI in Clin. Chem. 25, 353 (1979). Now, the molecules known to date are far from possessing all these properties.

The fluorescence of certain rare earth chelates has been known for many years through the work relating to their application in the field of lasers (A. P. B. SINHA, Spectroscop. Inorg. Chem. 2, 255 (1971)).

These complexes are formed of:

firstly a chelating molecule possessing an electron system capable of populating the triplet state $T_1$ by inter-system crossing after excitation of the singlet state $S_1$ following the absorption of luminous energy; and secondly a rare earth ion which, in the case of fluorescence applications, possesses a strong ion fluorescence intensity (Eu, Tb) or a moderate intensity (Sm, Dy), and whose resonance level is populated by the transfer of non-radiant energy from the triplet state of the complexing agent.

In order to obtain a strong fluorescence of the rare earth chelate, it is necessary for the triplet energy of the complexing molecule to be greater than that of the resonance level of the ion, and for it to have a sufficient life-time (preponderance of this type of deactivation compared with other processes such as phosphorescence and non-radiant deactivation, for example thermal deactivation).

In this case, after excitation in the absorption band of the chelate, a fluorescence characteristic of the rare earth ion is observed.

These compounds have great advantages in the field of detection by the measurement of fluorescence; for example, they are characterized by:

a large Stokes shift, a high molar absorption coefficient, $\epsilon$, relative to that of the rare earth, the possibility of simultaneous detection of several chelates by changing the rare earth, an emission spectrum characteristic of the rare earth (line spectrum, $\lambda$ of maximum emission $>500$ nm), and a long life-time (from a microsecond to a millisecond).

U.S. Pat. No. 4,058,732 describes a method of analytical spectroscopy by fluorescence which uses fluorescent molecules (rare earth chelates) having a relatively long life-time. In view of the fact that the diffusion due to the particles of the matrix, and the fluorescence of the majority of the organic molecules which make up the matrix, are short-lived phenomena (generally lasting less than 1 $\mu$sec.), the said patent recommends a pulsed excitation and a functionalized rare earth chelate for labeling the biological molecules to be identified, detection taking place between each pulsation and after a sufficiently long time for the undesired phenomena to have substantially decreased.

According to the prior art cited below, rare earth chelates theoretically satisfy all the conditions for forming a class of ideal fluorescent molecules, in particular as tracers for biological molecules in immunological determinations, in cytology and for cell classifiers:

U S. Pat. No. 4,058,732

SOINI, Clin. Chem. 25, 353 (1979)

L. M. VALLARINO et al. in Automation of Uterine Cancer Cytology 2, Proceedings of 2nd Int. Conf., G. L. WIED, G. F. GAHR and P. H. BARTEL, Editors, Tutorials of Cytology, Chicago LL 1977.

Now, in practice, it is found that the chelates used hitherto do not have all the following properties required by these applications, these being mainly:

a high quantum yield of fluorescence and a high molar absorption coefficient, a suitable triplet energy of the chelating agent, non-inhibition by the solvent (water or other solvent) or by molecules present in the medium in which the measurement is made, ease of functionalization for the purpose of coupling with molecules of biological interest or other molecules, selectivity of the chelation in favor of the rare earth and at the expense of other cations which may be present in large quantities in the measurement medium, solubility in water under the conditions of application of the immunological determinations, and a high stability, in particular at low dilution.

The β-diketone chelates described in U.S. Pat. No. 4,048,732 are only sparingly soluble in water and biological media, if at all, and their fluorescence is largely inhibited by water.

Other chelates have been proposed as tracers in immunological determinations; in particular, there may be mentioned the chelates derived from EDTA, HEDTA and DTPA, imidodiacetate and the like, and described for example in: Proc. Nat. Acad. Sci. U.S.A. 72, 4764 (1975), U.S. Pat. No. 4,374,120, European Patent Application No. A-0068875 and German Offenlegungsschrift No. 3 033 691. Their efficacy is assumed to originate from the high value of their stability constant, which is generally greater than $10^{10}$.

A criterion of this kind, based solely on thermodynamic considerations, is certainly not sufficient since it has been shown that the life-time of a Tb(III) EDTA complex is increased by the addition of apotransferrin (Biochem. 19, 5057, 1980), which is characteristic of a protein-chelate bond.

It has recently been recommended, when using tracers of the Eu(III) EDTA type such as those described in U.S. Pat. No. 4,374,120, to use a buffer containing DTPA in order to remove the free europium which has dissociated from the chelate, clearly proving the instability of such chelates Clin. Chem. 29, 60, 1983).

This state of the prior art shows that the rare earth chelates employed hitherto cannot be used at low dilution in aqueous media containing other cations or in biological media, and in particular in immunological determinations, and that criteria such as the kinetic stability (rate of dissociation of the complex) and the selectivity of formation of the rare earth complex should be taken into account.

It may be noted moreover that, by virtue of their high formation constant (in general $>10^{10}$), the majority of the chelates of the prior art have found an application in technical γ imagery, which uses γ-emitting heavy ions of relatively short life-time, obtained in dilute aqueous solutions. The fixation of the ion must then take place rapidly on the molecule of biological interest which carries the chelating agent; in particular, the rate of formation of the chelate must be high:

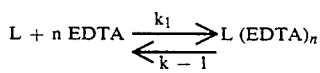

$k_1$ and $k-1$ being the rate constants of formation and dissociation respectively; at equilibrium, we have:

$$K = \frac{k_1}{k-1} = \frac{L(EDTA)_n}{[L][EDTA]^n}$$

For the complexes used hitherto, and for the reasons referred to above. the chelates which have always been used make it possible to obtain a high value of $k_1$ [≃$1.9 \cdot 10^{22}$ M$^{-1}$ min.$^{-1}$ for Eu$^{3+}$ EDTA—see J. inorg. nucl. Chem. 1971, 33, p. 127]. Consequently, for a given value of K, the dissociation rate constant is relatively large, which means that the rate of ion exchange between the chelate and the solution is relatively rapid.

Macropolycyclic rare earth complexes have now been found which possess excellent properties of selectivity and stability, especially of kinetic stability in aqueous media and biological media. These macropolycyclic complexes are particularly suitable as fluorescent tracers for biological substances in immunological detection or determination techniques using fluorescence. They are also suitable as reagents in luminescence reactions.

It has actually been found that it is possible to enhance the fluorescence of a rare earth ion in aqueous solution by complexing the ion with a macropolycyclic compound possessing a donor unit with a greater triplet energy than the emission level of the rare earth ion, and by exciting the donor unit.

Whereas the excitation of a rare earth ion produces a very weak fluorescence because rare earths generally have low molar absorption coefficients ϵ, excitation of the donor unit of the macropolycyclic compound defined below makes it possible to enhance the fluorescence characteristic of the rare earth ion. The rare earth complexes thus formed are excellent fluorescent tracers; furthermore, these are compounds which are stable in aqueous media and possess a very high selectivity in respect of rare earth ions.

In contrast to the chelates of the prior art, which are characterized by a high formation constant, the rare earth complexes according to the invention have as essential characteristic a high kinetic stability (low rate of dissociation). This characteristic is all the more important because the biological solutions used in immunological detection and determination methods generally contain proteins which themselves are also capable of fixing the rare earth ion. On the other hand, the rate of formation of the complexes of the invention is not critical. The formation of the rare earth ion complex, on the one hand, and the coupling of the resulting complex with the biological molecule, on the other, can be carried out separately. Consequently, the formation of the rare earth ion complex according to the invention can be carried out under non-biological conditions (use of organic solvents, possibility of supplying energy, time, etc.).

According to a first feature, the present invention therefore relates to the use of macropolycyclic rare earth complexes as fluorescent tracers, especially in immunological detection and determination methods, the said complexes consisting of at least one rare earth salt complexed by a macropolycyclic compound of the general formula:

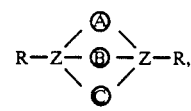    I in which Z is a trivalent or tetravalent atom such as nitrogen, carbon or phosphorus, R is nothing or represents hydrogen, the hydroxyl group, an amino group or a hydrocarbon radical, and the divalent radicals Ⓐ, Ⓑ and Ⓒ independently of one another are hydrocarbon chains which optionally contain one or more heteroatoms and are optionally interrupted by a heteromacrocycle, at least one of the radicals Ⓐ, Ⓑ or Ⓒ also containing at least one molecular unit or essentially consisting of a molecular unit, the said molecular unit possessing a greater triplet energy than the emission level of the complexed rare earth ion.

According to another feature, the invention also relates to a process for enhancing the fluorescence of a rare earth ion, which consists in complexing at least one rare earth ion with a macropolycyclic compound, such as defined above, possessing a molecular unit with a greater triplet energy than the emission level of the rare earth ion, and in exciting the complex thus formed at the absorption wavelength of the said molecular unit.

The rare earth complexes defined above are new compounds except for the europium and terbium complexes obtained with the macropolycyclic compound of the formula below:

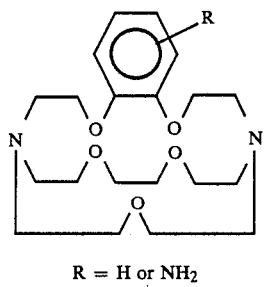

R = H or NH₂

Thus, the present invention also relates, by way of new compounds, to the rare earth complexes consisting of at least one rare earth salt complexed by a macropolycyclic compound of the formula I above, with the proviso that, if the rare earth salt is a europium or terbium salt, Z is nitrogen, Ⓐ is —(CH₂)₂—O—C₆H₃R—O—(CH₂)₂— and with R=H or NH₂, Ⓑ and Ⓒ are not simultaneously the radical —(CH₂)₂—O—(CH₂)₂—O—(CH₂)₂— in one case and the radical —(CH₂)₂—O—(CH₂)₂— in the other.

The hydrocarbon chains which form the radicals Ⓐ, Ⓑ and Ⓒ can contain 2 or more carbon atoms and can optionally be interrupted by one or more heteroatoms chosen from the group consisting of oxygen, sulfur or nitrogen atoms.

The preferred hydrocarbon chains for the purposes of the invention are polyether chains, in particular ethoxylated or polyethoxylated chains.

The molecular unit which constitutes an essential component of the macropolycyclic compound according to the invention is a triplet energy donor unit composed of molecules or groups of molecules possessing a greater triplet energy than the emission level of the complexed rare earth ion.

The energy transfer takes place from the triplet level of the donor unit to one of the emission levels of the complexed rare earth. For example, europium possesses the emission levels $^5D_0$ at 17270 cm$^{-1}$, $^5D_1$ at 19030 cm$^{-1}$ and possibly $^5D_2$, and terbium possesses the emission level $^5D_4$ at 20480 cm$^{-1}$.

The triplet energy donor units suitable for the purposes of the invention must possess a triplet energy which is greater than or equal to that of the emission levels of the rare earth ion. For example, in the case of the europium and terbium complexes according to the invention, the triplet level of the donor unit must be greater than 17270 cm$^{-1}$.

As the phenomenon of phosphorescence is due to the radiant deactivation of a triplet state, a preferred criterion for the donor units can be the phosphorescence emission wavelength of these units. For example, the chosen units will emit a phosphorescence at lower wavelengths (higher energies) than those corresponding to the population of the emission levels of the rare earth. In the present case, the phosphorescence wavelength of the donor unit will have to be below 580 nm.

It is pointed out that the complexes according to the invention can have one or more donor units, the said donor units constituting either all or part of the radicals Ⓐ, Ⓑ and Ⓒ.

Without implying a limitation, molecular units can be used are any triplet sensitizers having the requisite triplet energy, for example those described in European Patent Application No. A-0068875 or in Spectroscop. Inorg. Chem. 2, 255, 1971, these documents being cited in the present description by way of reference.

Particularly preferred molecular units for the purposes of the invention are phenanthroline, anthracene, benzene, naphthalene, biphenyl and terphenyl, bipyridines, biquinolines such as the bisisoquinolines, for example 2,2'-bipyridine, azobenzene, azopyridine, pyridine or 2,2'-bisisoquinoline.

The chains below may be mentioned in particular as examples of radicals Ⓐ, Ⓑ and Ⓒ containing an energy donor unit: —C₂H₄—X₁—C₆H₄—X₂—C₂H₄—; —C₂H₄—X₁—CH₂—C₆H₄—CH₂—X₂—C₂H₄—; X₁ and X₂, which can be identical or different, denote oxygen, nitrogen or sulfur;

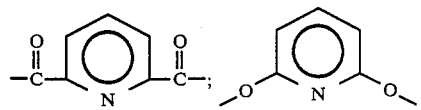

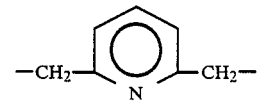

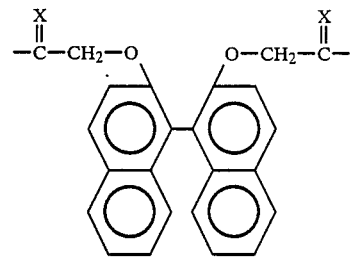

X being oxygen or hydrogen.

The macropolycyclic rare earth complexes according to the invention can be obtained by the conventional processes for the preparation of metal complexes, which consist in reacting the complexing compound with a compound donating the cation to be complexed. Processes of this type are described especially in U.S. Pat. Nos. 3,888,377, 3,966,766 and 4,156,683, which are cited in the present description by way of reference.

For example, the macropolycyclic complexes can be obtained by reacting a rare earth cation donor compound with the macropolycyclic compound having the characteristics defined above, each compound advantageously being in solution, preferably in the same solvent or in compatible solvents which are inert towards complex formation. In general, acetonitrile, DMSO or ethanol is used as the solvent.

The rare earth cation donor compound which can be used is any rare earth salt, advantageously a chloride an acetylacetonate or a nitrate.

The reaction is advantageously carried out at the boiling point of the solvent.

If the macropolycyclic complex formed is soluble in the reaction solvent, it is isolated from the solution by evaporation to dryness. If the macropolycyclic complex formed crystallizes from the reaction solvent, it is separated off by filtration or any other appropriate conventional means. The complexes thus obtained can be purified by crystallization.

The above reaction can also be carried out using a solution of the macropolycyclic compound and the cation donor compound in the crystalline form. A synergistic agent for protecting against deactivation can also be introduced into the coordination sphere of the cation, as described in J. Chem. Phys. 40, 2790 (1964) and 41, 157 (1964).

In the remainder of the present description, the macropolycyclic complexes according to the invention are also called "cryptates" and the macropolycyclic compound by itself is also called "cryptand". The nomenclature as defined by LEHN will be adopted below for denoting the cryptates and cryptands. For this purpose, reference may be made especially to the articles by J. M. LEHN in Struct. Bonding (Berlin) 16, 1, 1973 and Acc. Chem. Res. 11, 49 (1978).

All the rare earth ions are suitable for the purposes of the present invention. However, preference will be given to those which exhibit the most intense ion fluorescence, i.e. terbium and europium and, to a lesser extent, samarium and dysprosium.

As macropolycyclic compounds suitable for the purposes of the invention, it is possible to use the known cryptands, for example:

(1) The benzo-cryptands of the general formula:

$$N \underset{\underset{©}{|}}{\overset{\overset{Ⓐ}{|}}{-Ⓑ-}} N,$$

in which Ⓐ, Ⓑ and Ⓒ independently of one another represent the groups $2_B$, 2 and 1, which have the following meanings:

$2_B = -C_2H_4-X_1-C_6H_4-X_2-C_2H_4-$ or
$\phantom{2_B =} -C_2H_4-X_1-CH_2-C_6H_4-CH_2-X_2-C_2H_4-$ $2 \phantom{_B} = -C_2H_4-Y_1-C_2H_4-Y_2-C_2H_4-$ $1 \phantom{_B} = -C_2H_4-Z-C_2H_4-$ in which $X_{1,2}$, $Y_{1,2}$ and Z each represent a heteroatom chosen from the group consisting of oxygen, sulfur and nitrogen, it being possible for $X_1$ and $X_2$, and $Y_1$ and $Y_2$, to be identical or different.

Examples of such cryptands which may be mentioned are those in which the units Ⓐ, Ⓑ and Ⓒ are respectively composed as follows:

Ⓐ Ⓑ Ⓒ = $(2_B11)$; $(2_B21)$; $(2_B22)$; $(2_B2_B2)$; and the compound of the formula:

(2) The cryptands containing nitrogen heterocycles, such as those described in JACS 99, 4583 (1977), of the formula I in which:

Ⓐ and Ⓑ, which are identical, represent the polyethoxylated chain of the formula $-(CH_2)_2-O-(CH_2)_2-O-(CH_2)_2-$, and Ⓒ is a hydrocarbon chain containing a nitrogen heterocyclic as the energy donor unit. Examples of such compounds which may be mentioned in particular are the compounds below:

(22)pyridinamide (22)pyridinamide (22)bipyridine

(22) bipyridinamine (22)azopyridine (3) The cryptands containing several nitrogen heterocycles as donor units, such as the compound of the formula below:

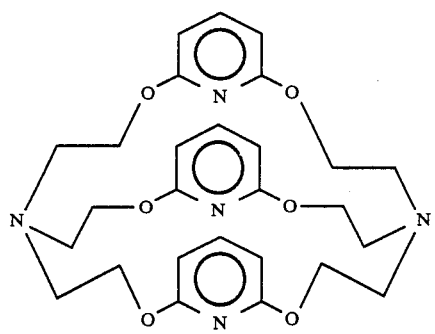

described in J. Am. Chem. Soc. 1979, 101, p. 1047.

(4) The polycyclic cryptands containing aromatic units, for example the compounds corresponding to the formula below:

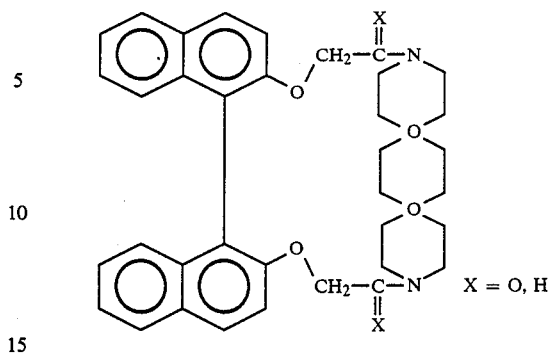

X = O, H or the compounds of the formula I in which the hydrocarbon chain carrying the donor unit or units is interrupted by a heteromacrocycle, such as the compounds of the formulae below:

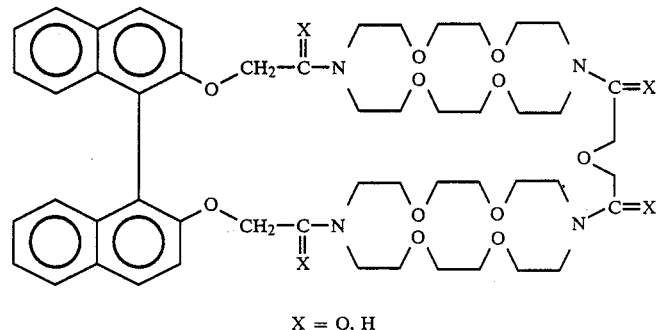

X = O, H

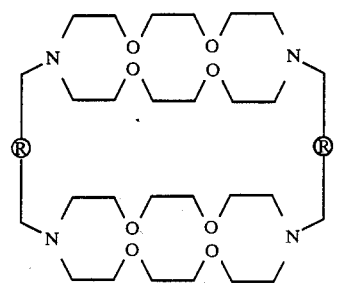

R = 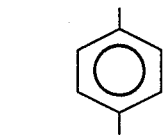

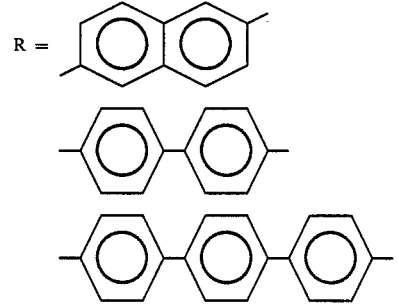

Such compounds are described especially in: Angew: Chemie 86, 443 (1974); Tet. letters 21, 941 (1980) and Chem. Comm. 833, 1981.

Other cryptands which can be used are the macropolycyclic compounds of the formula I above in which the molecular unit or units possessing a triplet energy greater than the energy of the rare earth to be cryptated are chosen from the group consisting of phenanthroline, anthracene, bipyridines and the bisquinolines, possibly substituted is appropriate positions and by groups capable of increasing the efficiency of the transfer of energy or to modify the excitation spectrum of the rare earth cryptate. [J. Phys. Chem. 1964, vol. 68, p. 3324]. One example of such groups is the phenyl group.

In these new macropolycyclic compounds, at least one of the radicals Ⓐ, Ⓑ or Ⓒ preferably corresponds to one of the formulae below:

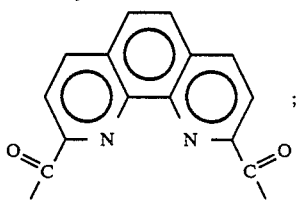

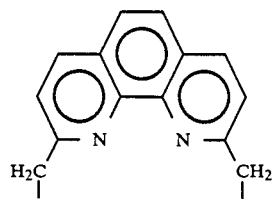

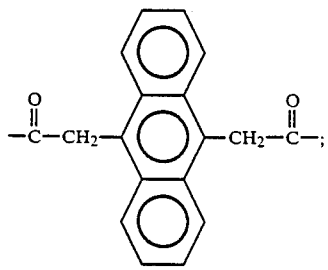

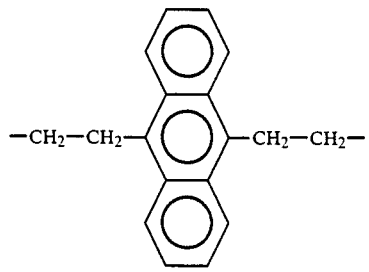

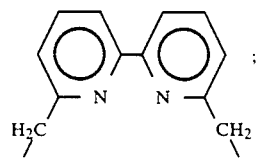

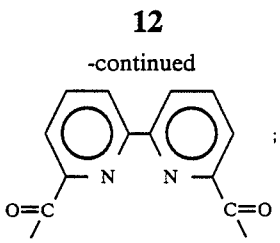

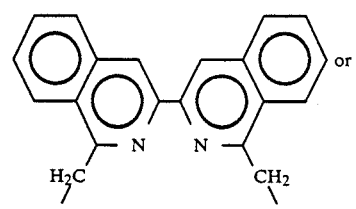

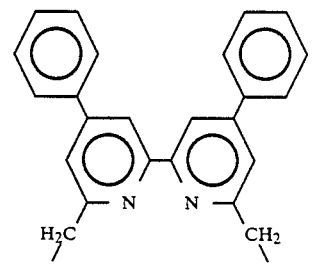

A particular class of these macropolycyclic compounds consists of the compounds of the formula I in which z is nitrogen, Ⓐ and Ⓑ are two mono- or polyethoxylated chains, preferably diethoxylated, and Ⓒ corresponds to one of the formulae above.

These new macropolycyclic compounds also include the compounds of the formula I in which Ⓐ and Ⓑ each represent the group:

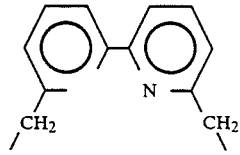

and Ⓒ is one of the following groups:

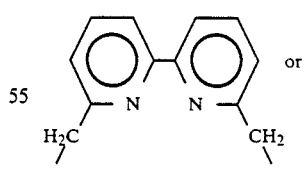

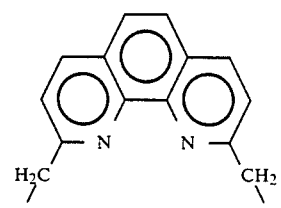

-continued

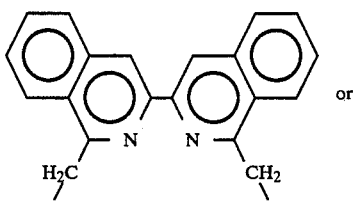

or

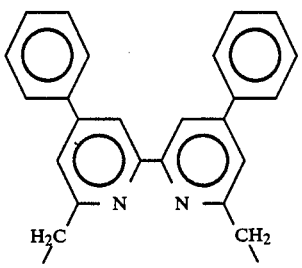

Another particular class of these new macropolycyclic compounds is constituted by the compounds of the formula I in which Z is nitrogen and Ⓐ, Ⓑ, and Ⓒ are identical and represent one of the above indicated heterocycles, namely the 2,2'-bipyridine and phenanthroline.

The macropolycyclic compounds of the formula I in which the molecular moiety or moieties are phenanthroline, anthracene, bipyridines or quinolines are new compounds with the exception of the compounds of formula I in which Ⓐ and Ⓑ are each a chain of the formula —(CH₂)₂—O—(CH₂)₂—O—(CH₂)₂— and Ⓒ is the group of the formula

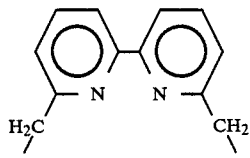

or the group of formula

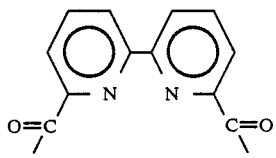

which are described in Chem. Ber. 111, pages 200–204 (1978).

The macropolycyclic compounds of the formula I can be obtained by known chemical processes involving mainly condensation and/or addition reactions.

The processes described in French Pat. No. 70 21079 (2052947) and U.S. Pat. Nos. 3,888,877, 3,966,766 and 4,156,683 may be mentioned in particular as examples of such processes. These processes are especially suitable for the preparation of compounds of the formula I in which Z is nitrogen or phosphorus.

To obtain compounds of the formula I in which Z is carbon and R is as defined above, analogous condensation processes will be used.

In all cases, it suffices to use, as starting materials, chemical compounds each containing one of the radicals Ⓐ, Ⓑ or Ⓒ and ends groups capable of being su or containing radicals which can easily be removed.

By way of example, it may be indicated that the compound of the formula I in which Z is carbon, R is the hydroxyl group and Ⓐ, Ⓑ and Ⓒ each represent 2,2'-bipyridine can be obtained by condensing 6,6'-dilithiobipyridine with 6,6'-dicyano-2,2'-bipyridine, hydrolyzing the cyano group of the macrocycle thus obtained and condensing the resulting product with 6,6'-dilithiobipyridine.

In a preferred procedure, the new macropolycyclic compounds of the formula I in which Z is nitrogen and Ⓐ and Ⓑ are polyethoxylated chains can be obtained by reacting:

the nitrogen macrocycle consisting of the two polyethoxylated chains, with the hydrocarbon chain containing the said molecular unit, the said chain having cleavable end groups such as, for example, halogeno groups.

This coupling reaction is advantageously carried out in an anhydrous solvent, for example dimethyl sulfoxide (DMSO) or acetonitrile, if appropriate in the presence of a reducing agent, such as sodium hydride or sodium carbonate. The macropolycyclic compound is then obtained in the form of a sodium salt.

The reaction is preferably carried out at a temperature below the boiling point of the solvent, for example at between 60° and 100° C.

It is possible, in order to obtain the free macropolycyclic compound to react said sodium salt with silver nitrate to form the macropolycyclic silver complex, which is thereafter treated with a stream of H₂S. The formed precipitate is then neutralized with a solution of (N(CH₃)₄OH and extraced with methylene chloride.

It will be noted that the macropolycyclic rare earth complex according to the invention may be obtained from the free complex or from a salt thereof, such as the sodium salt for example.

In the above process, any one of the nitrogen-containing monocyclic macrocycles described in U.S. Pat. No. 3,966,766 can advantageously be used as the macrocycle, the preferred compounds being: 1,7,10,16-tetraoxa-4,13-diazacyclooctadecane of the general formula:

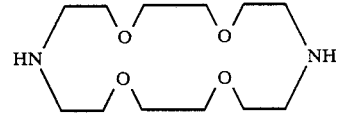

or 1,7,16-trioxa-4,13-diazacyclodecane of the general formula:

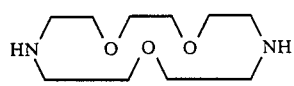

It is pointed out that the preferred complexes according to the invention, obtained from the above macrocycles, can be considered as derivatives of cryptates of the type 222 or 221, in which the ether units in at least one of the hydrocarbon chains have been substituted by energy donor units (in general aromatics or polyaromatics possibly containing heteroatoms).

The europium cryptates of type 222 or 221 have very low rates of dissociation in aqueous solutions, although their formation constant is relatively low ($K=10^{6.8}$ and $10^{5.9}$ or the cryptates 221 and 222 respectively—Inorganic Chem. 1981, 20, p. 616 and J.A.C.S. 1980, 102, p. 2278. Such cryptates do not satisfy the stability criteria defined in the prior art. On the other hand, substitution of the ether units by energy donor units, which provides the preferred complexes according to the invention, does not modify the dissociation characteristic of these cryptates but makes it possible, by excitation of the energy donor unit in its absorption band, to obtain a greatly enhanced fluorescence characteristic of the cryptated rare earth.

If the rare earth cryptates forming the subject of the present invention are used specifically to label biologically active molecules with the aid of a covalent bond, they can be substituted on one or more of their constituent atoms by one or more sufficiently accessible substituents possessing one or more molecular units which permit covalent coupling with the biological molecule under operating conditions compatible with its biological integrity.

Non-limiting examples of these molecular units which may be mentioned are alkylamino, arylamino, isothiocyano, cyano, isocyano, thiocyano, carboxyl, hydroxyl, mercapto, phenol, imidazole, aldehyde, epoxide, thionyl halide, sulfonyl halide, nitrobenzoyl halide, carbonyl halide, triazo, succinimido, anhydride, halogenoacetate, hydrazino, dihalogenotriazinyl and other radicals (Biol. Chem. 245, 3059 (1970). The length of the arm bonding the macrocyclic complex to the molecule of biological interest can vary from 1 to 20 atoms, for example, and can contain carbon atoms as well as heteroatoms such as N, O, S and P. The invention therefore also relates to the biological complexes consisting of a biological molecule which is associated by coupling or adsorption with a macropolycyclic complex according to the invention.

The coupling can be carried out using any of the reagents described for this purpose in the literature and the labeled molecule can be separated from the unreacted macropolycyclic complex by any suitable means of separation (for example gel filtration).

Among the molecules of biological interest which can advantageously be labeled with the rare earth cryptates forming the subject of the present invention, there may be mentioned, without implying a limitation, antigens, antibodies, monoclonal antibodies, fragments and antibody-fragment combinations, drugs, receptors, hormones, hormone receptors, bacteria, steroids, amino acids, peptides, vitamins, viruses, nucleotides or polynucleotides in hybridization methods, enzymes and their substrates, lectins, nucleic acids, DNA and RNA.

The macropolycyclic rare earth complexes according to the present invention find an important application as fluorescent tracers in immunological determinations, either in the so-called methods of determination by competition or in the so-called methods of determination by excess, in the homogeneous or heterogeneous phase, the said determinations being described in the prior art (LANDON, Ann. Clin. Biochem. 1981, 18, p. 253 and SOINI, Clin. Chem. 25, 353, 1979).

In the heterogeneous methods, it is possible advantageously to use:

tubes coated with antibodies specific for the substance to be determined, and to read off the fluorescence by the methods described above, directly through the tube Clin. Chem. 29, 60, 1983).

or a different solid phase, in particular a narrow strip or a gelatinous film on which a medium containing a specific antibody has been deposited beforehand, the fluorescence being read off at a different angle from the excitation and the reflection of the exciting wave or directly through the support, if this is transparent.

Because of the line spectrum of these tracers, it is also possible to detect several antigens simultaneously either by using cryptates of different rare earths whose fluorescence lines do not overlap (for example Tb and Eu), or by using conventional fluorescent tracers (fluorescein or rhodamine) and tracers according to the present invention.

Another application relates to immunochemistry, where the fluorescence of the labeled cell is detected by microscopy in the manner described by R. C. NAIRN in "Fluorescent Protein Tracing, Longman Group Ltd.", 1976, which also has the possibility of carrying out multi-detection.

Another application of the rare earth complexes according to the invention relates to cytology and cell classifiers, where the use of a tracer having a line spectrum at high wavelength, coupled with the use of conventional tracers, makes it possible to perform multi-parameter analyses.

Furthermore, with a given cryptand and different rare earth ions, it is possible, with a single exciting wavelength, which is that of the molecular unit transferring the energy and which can be generated with a single source (for example a laser), to obtain two fluorescence line spectra characteristic of the two cryptated ions (for example Tb and Eu) and thus disclosing the respective biological molecules to which the cryptates are fixed.

Another application relates to the use of the rare earth cryptates according to the present invention in the field of genetic engineering, for example as indicators in hybridization reactions such as those described in European Patent Applications Nos. A-0 070 685 and A-0 070 687.

The invention will now be described in greater detail by means of the non-limiting illustrative examples below.

EXAMPLE 1

A—Preparation of (22)phenanthroline (hereafter called: (22)phen)

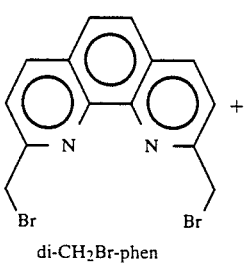

di-CH$_2$Br-phen

-continued

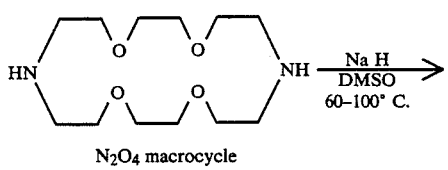

N₂O₄ macrocycle

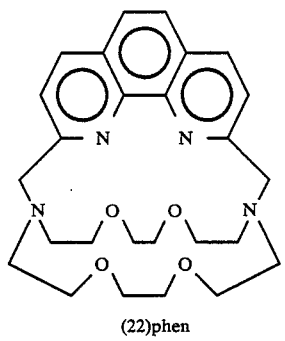

(22)phen

The solvent used in this synthesis is DMSO, which was dried for several days over a 4 Å molecular sieve and, if appropriate, distilled in vacuo.

1 mmol (366 mg) of dry and freshly chromatographed dibromomethylphenanthroline compound di-CH₂Br-phen) was dissolved in 10 to 20 ml of DMSO. It was transferred to a dry dropping funnel; the volume was made up to 100 ml with dry DMSO.

100 to 200 mg of NaH in oil (FLUKA) were placed in a dry round-bottomed flask; 5 ml of dry toluene (or hexane) were added to the mixture, which was left to settle. The solution was evaporated in vacuo (1 torr) for 1 hour. The NaH was redissolved in 20 ml of dry DMSO (evolution of H₂), with heating to 50° C. if appropriate.

1 mmol of the N₂O₄ macrocycle (262 mg) was dried and 10 to 20 ml of dry DMSO were added.

The solutions of NaH and N₂O₄ macrocycle were each introduced into a dropping funnel and the volume was made up to 100 ml with dry DMSO.

100 ml of dry DMSO were placed in a three-necked round-bottomed flask. This flask was equipped with the two dropping funnels, a reflux condenser and a drying system (silica gel). The flask was heated to 60°–100° C., with magnetic stirring.

The contents of the two dropping funnels were simultaneously added dropwise over a period of 1 to 2 hours.

The reaction mixture was heated for 1 hour after the reactants had been added. The mixture was then distilled in vacuo to remove the solvent.

It is possible to add a small quantity of water in order to remove the hydrides and the bases.

The reaction mixture was reduced to dryness to give a dry or pasty red residue.

100 to 200 ml of CH₂Cl₂ were added; the paste was triturated at room temperature for at least 30 minutes. The residue was filtered off and washed. The organic liquid phase was retained and evaporated in vacuo. The residue obtained was dried in vacuo (1 torr, at least 30 minutes).

100 ml of ethyl ether were added to the residue, the components were mixed and the mixture was left to settle; this operation was repeated 3 to 4 times.

To remove the remainder of the monocyclic N₂O₄ macrocycle more completely, 50 ml of hexane and 1 ml of CH₃OH were added to the residue: the solution was evaporated in vacuo (gentle heating until turbidity appeared; the solution was decanted and the operation was repeated several times.

The red residue was tested by slab chromatography (Polygram Alox N/UV₂₅₄ from Macherey-Nagel); migration in the medium CH₂Cl₂/CH₃OH 9/1 gave the following values:

| (22)phen | Rf = 0.4–0.8 |
| Monocyclic N₂O₄ macrocycle | Rf = 0.2–0.5 |

The residue was chromatographed on a column (20 cm, φ 15 cm) packed with neutral activated aluminum oxide 90 of 70–230 mesh (Merck), the eluent consisting of the following mixtures: CH₂Cl₂/CH₃OH (5%), CHCl₃/C₂H₅OH (5%), CH₃OH/hexane 9/1. Yields from 12 to 35% according to the operating conditions.

This gave the sodium salt of (22)phen, of the formula [Na⁺C(22)phen-Br.H₂O], the elemental analysis of which was as follows:

| found: | C 53.00 | H 6.21 | N 9.44 |
| calculated: | C 53.16 | H 6.18 | N 9.55 |

B—Formation of the complex [Eu³⁺C(22)phen]

0.07 mol (19.4 mg) of anhydrous EuCl₃ was dissolved in 4 ml of dry CH₃CN and the solution was heated under reflux for 1 hour 30 minutes. 35 mg of the previously obtained sodium salt of (22)phen in 2.5 ml of CH₃CN were added. The mixture was heated under reflux for 2 hours 30 minutes. After the mixture had been left to stand overnight at 4° C., the yellow precipitate was filtered off.

The precipitate collected (11 mg) exhibits a strong fluorescence and this also applies when it is in solution in H₂O and CH₃OH (UV 254 nm).

No change in the excitation and emission spectra was observed after three months in aqueous solution at a concentration below 10⁻⁴ mol/liter.

EXAMPLE 2

A—Preparation of (22)phenanthrolinamide (hereafter called (22)phenamide)

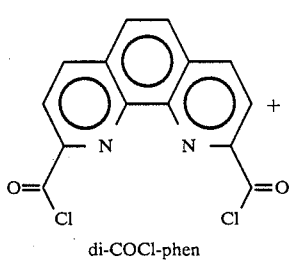

di-COCl-phen

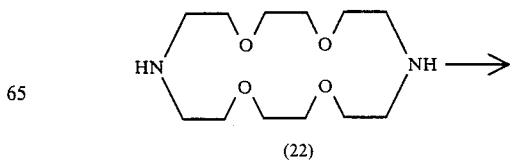

(22)

-continued

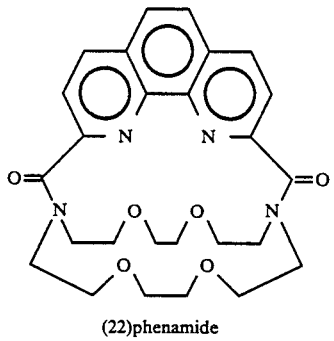

(22)phenamide

The solvent used in this synthesis is acetonitrile distilled over $P_2O_5$. The process was carried out in a dry glass apparatus.

305 mg of dry recrystallized di-COCl-phen (1 mmol) were dissolved in 50 ml of $CH_3CN$: after one night, the solution was filtered and transferred to a dropping funnel; the volume was made up to 90 ml with $CH_3CN$.

524 mg of (22) (2 mmol) were dried in (<1 torr; overnight). The product was dissolved in 90 ml of $CH_3CN$ and transferred to a dropping funnel The two dropping funnels were fitted to a 2 to 3 liter round-bottomed flask containing 1 liter of $CH_3CN$. The two reactants were added simultaneously over a period of 2 hours to 2 hours 30 minutes, with rapid stirring (magnetic). Stirring was continued for 30 minutes after the addition. The solvent was removed in vacuo at 50° C. The residue was dried for at least 1 hour at P<1 torr. The residue was mixed for 30 minutes in 300 ml of $CH_2Cl_2$ and filtered off. The filtrate was evaporated to dryness. The residue was chromatographed on neutral activated Alox 90 (column 30 cm, $\phi$ 1.5 cm), the eluent being $CH_2Cl_2$ containing 1% of $CH_3OH$. The first product eluted was recovered.

310 mg of (22)phenamide were recovered with a yield of 63%. The product was recrystallized from a mixture of toluene/hexane 1/1.

Melting point: 300°–302° C.
IR amide band at 1630 $cm^{-1}$
Mass spectrum: M+ at 494 for MW=494.55

| Elemental analysis: $C_{26}H_{30}N_4O_6$ | | | |
|---|---|---|---|
| | C | H | N |
| Calculated: | 63.15 | 6.11 | 11.33 |
| Found: | 59.8 | 5.7 | 10.5 |
| | 59.9 | 5.9 | 10.6 |

B—Formation of the complex [$Eu^{3+}$C(22)phenamide]

45 mg (0.17 mmol of anhydrous $EuCl_3$ were dissolved in 10 ml of dry $CH_3CN$. A solution of 80 mg (0.16 mmol) of (22)phenamide in 2 ml of $CH_2Cl_2$ was heated under reflux for 3 hours, 50 ml of $CH_3CN$ were added and the mixture was heated to the boiling point of the $CH_3CN$ ($CH_2Cl_2$ is removed by evaporation).

Then the solution of $Eu^{3+}$ was added.

The mixture was heated under reflux for 2 hours and then left to stand at room temperature. The white precipitate was recovered by filtration (50 mg). It exhibited a strong red fluorescence ($\lambda$ excitation: 254 nm) and the same applied in solution in $H_2O$, $CH_3OH$ and DMSO.

| Elemental analysis for EuC(22)phenamide(OH)Cl$_2$.3H$_2$O $C_{26}H_{37}N_4O_{10}Cl_2Eu$ MW = 788.47 | | | |
|---|---|---|---|
| | C | H | N |
| Calculated: | 39.61 | 4.73 | 7.11 |
| Found: | 40.1 | 4.9 | 7.2 |
| | 40.3 | 4.8 | 7.1 |

No changes in the excitation and emission spectra of this complex were observed after three months in aqueous solution at a concentration below $10^{-4}$ mol/liter.

EXAMPLE 3

Preparation of (22)anthracenamide

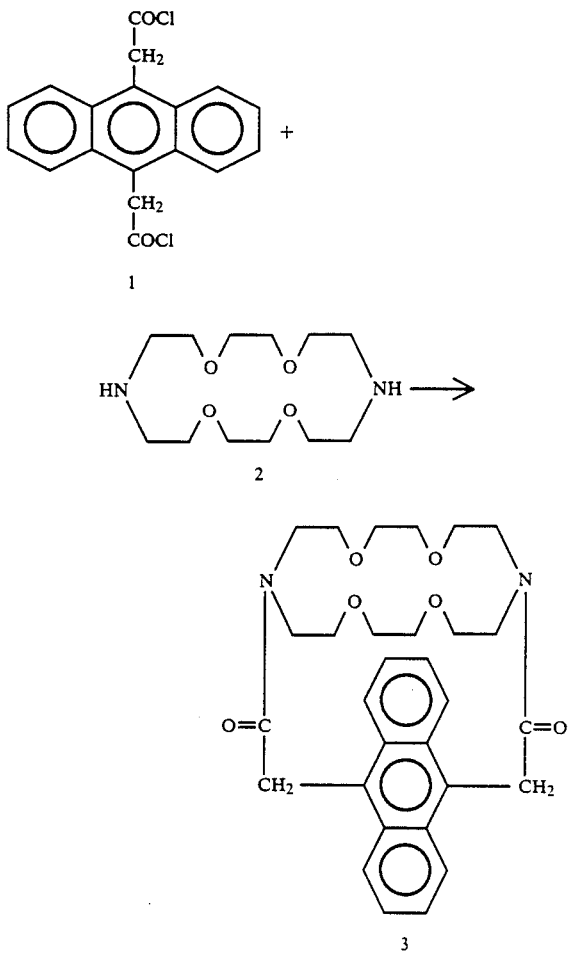

In this example, the method of high dilution is used.

0.564 g of the acid dichloride 1 (1.7 mmol) was dissolved in 70 ml of anhydrous $CH_2Cl_2$ and the solution was introduced into a 100 ml dropping funnel;

0.446 g of the macrocycle (22), i.e. 1.7 mmol, and 0.47 ml of triethylamine (2×1.7 mmol) were also dissolved in 70 ml of anhydrous $CH_2Cl_2$ and the solution was introduced into a 100 ml dropping funnel.

0.4 ml of toluene and 0.15 liter of anhydrous methylene chloride were introduced into a 3 liter three-necked flask. The two reactants prepared above in the dropping funnels were introduced simultaneously into the flask over a period of 5 hours (14 ml/hour).

The organic phase was collected, concentrated to a few milliliters and then transferred to a column of SiO₂ under pressure (column diameter 3.5 cm; height 17 cm: eluent CH₂Cl₂/1% of methanol).

This gave a pale yellow, crystalline fluorescent product.

Yield: 45%

Thin layer chromatography (TLC): solvent CH₂Cl₂/2% of methanol; SiO₂; Rf=0.6

| ¹H NMR: solvent CDCl₃/CD₂Cl₂ 5/5, at 200 MHz | | |
|---|---|---|
| ppm | 2.53 (m) | |
| | 2.93 (m) ⎫ | |
| | 3.18 (m) ⎬ | 24 H, HCH₂ + OCH₂ crown |
| | 3.42 (m) ⎭ | |
| | 4.02 (d) | |
| | δ$_A$ = 4.62 | J$_{AB}$ = 16 Hz 4H OCCH₂N |
| | δ$_B$ = 5.03 | |
| | 7.6 (m) | 4H ⎫ |
| | 8.43 (d) | 2H ⎬ aromatic |
| | 8.82 (d) | 2H ⎭ |
| Microanalysis: C₃₀H₃₆O₆N₂ | | |
| Calculated: | C 69.20  H 6.97  N 5.38 | |
| Found: | C 69.07  H 7.00  N 5.22 | |

Molecular weight: 520.55

The acid dichloride 1 used as the starting material in this example can be obtained by the processes described by M. W. Miller et al. in R. W. Amidon and P. O. Tawney, J.A.C.S. 77; 2845 (1955) or by B. M. Mikhailov, Izvest. Akad. Nank. SS. Osdel Khim. Nank. 1948, 420-6; CA 42, 6350.

EXAMPLE 4

Preparation of (22)anthracene

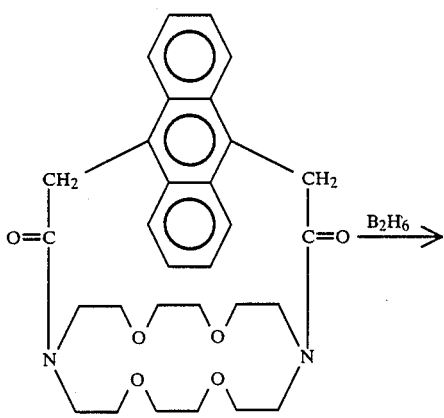

3

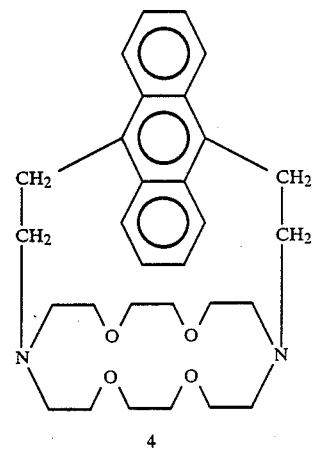

4

380 mg of the diamide 3 (0.73 mmol) were partially dissolved in 20 ml of anydrous THF contained in a round-bottomed flask.

The flask, fitted with a reflux condenser, was placed under an argon atmosphere and 8 ml of 1.1M B₂H₆ in anhydrous THF were added at room temperature.

The whole reaction mixture was kept under reflux overnight and the excess diborane was then destroyed at 0° C. with a few drops of distilled water.

The solvents were evaporated off and 40 ml of a 6N solution of HCl were added to the residual white solid.

The solution was heated under reflux for 30 hours under an argon atmosphere and became dark green.

It was left to cool, the water was then evaporated off and the resulting solid was pumped dry with a vane pump for 1 hour and was then dissolved in 50 ml of distilled water; 50 ml of CH₂Cl₂ were added, the two phases were shaken and the aqueous phase was then separated off and rendered basic at 0° C. with an aqueous solution of LiOH to pH 13; a solid precipitated. A further 50 ml of CH₂Cl₂ were added and the two phases were shaken and left to settle. The organic phase was recovered and dried over MgSO₄.

The crude product was transferred to a column of alumina and eluted with CH₂Cl₂/1% of methanol. A pure crystalline product was recovered on a TLC Plate.

Yield: 62–70%

TLC: Al₂O₃; eluent CH₂Cl₂/6% of MeOH; Rf: 0.33

Melting point: >260° C.

¹³C NMR: solvent CDCl₃
ppm  25.2 (aromatic CH₂)

54.3 ⎫
56.3 ⎬ NCH₂ macrocycle + branch 69.3 ⎫
70.0 ⎬ OCH₂ macrocycle

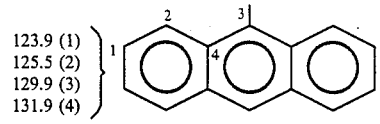

123.9 (1)
125.5 (2)
129.9 (3)
131.9 (4)

¹H NMR: solvent CDCl₃
ppm  2.39 (t) 8H NCH₂ macrocycle 2.55 and 2.76 (m) — 2 × 4H OCH₂ N  O -continued

| 2.89 and 3.19 (m) — 2 × 4H | OCH₂O |
| 3.03 and 3.82 (t) — 2 × 4H | —CH₂—CH₂ |
| 7.47 and 8.31 (AB) — 4H | } aromatic H |
| 7.50 and 8.36 (AB) — 4H | |

Microanalysis: C₃₀H₄₀O₄N₂ (molecular weight 492.6)
Calculated:    C 73.13    H 8.18    N 5.6
Found:         C 73.06    H 8.04    N 5.2

The complex [Eu³⁺⊂(22)anthracene] was prepared by following the produced described in Example 1.

EXAMPLE 5

Preparation of the macropolycyclic compound of the formula (7) and the corresponding europium complex A—Preparation of 6,6'-bis-bromomethyl-2,2'-bipyridine molecular weight 184
C₁₂H₁₂N₂ molecular weight 342
C₁₂H₁₀N₂Br₂

A mixture of 6,6'-dimethyl-2,2'-bipyridine (2.76 g, 15 mmol) and N-bromosuccinimide (5.10 g, 28.6 mmol) in CCl₄ (150 ml) is heated under reflux for 30 minutes. Benzoyl peroxide (30 mg) was subsequently added to the mixture, this was heated under reflux again for 2 hours and the succinimide was then filtered off. The solution was cooled to 0° C. and the solid was filtered off and washed with methanol to give the bisdibromide in the form of a white crystalline solid (1.65).
Yield 32%; melting point 180°–181° C.

The CCl₄ solution was concentrated and chromatographed on a column (silica gel) by elution with a mixture of methylene chloride/methanol 98/1 to give:
6,6'-bis-dibromomethyl-2,2'-bipyridine 0.9 g, 12%
6,6'-bis-bromomethyl-2,2'-bipyridine 1.38 g, 27%
6-methyl-6'-bromomethyl-2,2'-bipyridine 0.55 g, 14%

B—Preparation of the macropolycyclic compound

A mixture of the bis-hipyridine macrocycle of the formula (5) (0.15 g, 0.38 mmol) (described in J. Org. Chem. 1983, 48, 4848) and Na₂CO₃ (0.4 g) in acetonitrile (200 ml) was heated to the reflux temperature and a solution of 6,6'-bis-bromomethyl-2,2'-bipyridine (0.12 g, 0.38 mmol) was then added over a period of 3 hours. The mixture was subsequently heated under reflux for 20 hours. The Na₂CO₃ was filtered off and the filtrate was evaporated. The residue was filtered on a short column of alumina by elution with CH₂Cl₂/MeOH 98/2 to give the sodium salt of the tris-bipyridine macrobicyclic compound in the form of a white solid (0.16 g : 73%); melting point above 270° C.).

| Microanalysis: C₃₆H₃₀N₈, Na Br (677,6) | | |
|---|---|---|
| calculated: | C 63.81 | H 4.46 | N 16.53 |
| found: | C 63.79 | H 4.48 | N 16.49 |
| NMR ¹H: solvent CDCl₃ | | |

3.85 (s, 6CH₂);
7.33 (dd, J = 7,2; 1,2; 6H; H—C(5); H—C(5'))
7.82 (t, J = 7.2; 6H; H—C(4); H—C(4'))
7.90 (dd; J = 7.2; 1.2; 6H; H—C(3); H—C(3'))

A mixture of silver nitrate AgNO₃(15 mg, 0.08 mmol) and of the sodium salt obtained above (20 mg, 0.03 mmol) was heated with 5 ml of CH₃OH for 30 minutes. The methanol was evaporated and the resulting complex was purified over a column of silica gel with CH₂Cl₂/CH₃OH as eluent (96/4).

The resulting silver complex (20 mg) was dissolved in a water-methanol mixture (1:1–5 ml) and treated with a stream of H₂S for 15 minutes. The formed precipitate was centrifuged and the solution neutralized with N(CH₃)₄OH 0.1N and extracted with methylene chloride (3.5 ml). The solution was dried on MgSO₄ and evaporated; the resulting solid was filtered on silica gel $CH_2Cl_2$: $CH_3OH$ (96:4) to give the free complex (13 mg; 86%) with the following characteristics:

| NMR $^1$H: solvent $CDCl_3$ | |
|---|---|
| 3.82 | (s, 12H, $CH_2$) |
| 7.44 | |
| 7.78 | ABX System J = 8; 7.5 and 0.9 Hz |
| 7.83 | |

Microanalysis: $C_{36}H_{30}N_8$ (574.7)

| | | | |
|---|---|---|---|
| Found: | 75.37 | H 4.98 | N 19.41 |
| calculated: | C 75.24 | H 5.26 | N 19.50 |

The macropolycyclic compound obtained was used to prepare the complex [$Eu^{3+}$C(tris-bipyridine macropolycycle)] by following the procedure described in Example 1.

EXAMPLE 6

Preparation of the bis-bipyridinephenanthroline macropolycyclic compound of the formula (9) and the corresponding europium complex

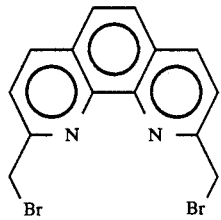

$C_{14}H_{10}Br_2N_2$

8

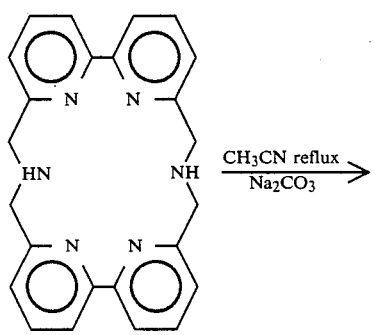

$C_{24}H_{22}N_6$

5

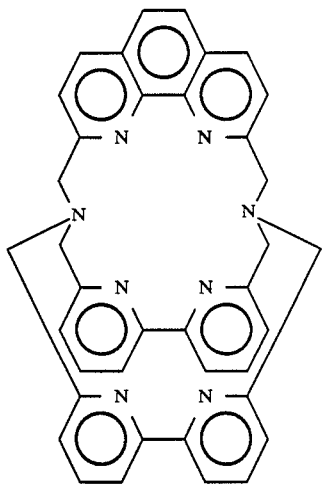

$C_{38}H_{30}N_8$

9

0.158 mmol of the bis-pyridine macrocycle (5) was weighed into a 500 ml two-necked round-bottomed flask. 0.75 mmol of $Na_2CO_3$ (approx 5-fold excess) and 105 ml of freshly distilled $CH_3CN$ were added. The mixture was heated under reflux for 30 minutes, with magnetic stirring.

An equimolecular dibromophenanthroline solution in 100 ml of acetonitrile was then added dropwise.

Refluxing and magnetic stirring wet continued throughout the rather slow addition (2 hours 10 minutes).

The mixture was then heated for a further 18 hours under the same conditions. The solution obtained was evaporated to dryness. The crude product, dissolved in $CH_2Cl_2$, was washed with water. (Thin layer chromatography on alumina:eluent $CH_2Cl_2$/MeOH 90/10.)

This crude product was purified on a column of standardized alumina (activity II-III), the eluent being $CH_2Cl_2$/MeOH 98/2.

| Microanalysis: $C_{38}H_{30}N_8$, Na Br, $H_2O$ (719,6) | | | |
|---|---|---|---|
| calculated: | C 63.42 | H 4.45 | N 15.57 |
| found: | C 62.77 | H 4.46 | N 15.31 |

RMN $^1$H: solvent - $CDCl_3$ 3.91 (s, 8H, $CH_2$-bpy)
4.07 (s, 4H, $CH_2$-phen)
7.36 (dd, J = 7.2; 1,3; 4H; H—C(5); H—C(5') of the bipyridine)
7.64 (d, J = 8.2; 2H; H—C(3), H—c(8) of phenanthroline,
7.78 (s, 2H, H—C(5), H—C(6) of phenanthroline
7.83 (t, J = 7.2; 4H; H—C(4); H—C(4') of bipyridine
7.91 (dd, J = 7.2; 1,3; 4H; H—C(3); H—C(3') of bipyridine
8.27 (d, J = 8.2; 24; H—C(4);
4-C(7) of phenanthroline.

The macropolycyclic compound thus obtained was used to prepare the complex [$Eu^{3+}$C(bis-biyrinephenanthroline macropolycycle)] by following the procedure described in Example 1.

The excitation and emission wavelengths characteristic of this complex are shown in the Table below.

EXAMPLE 7

The macropolycyclic complexes below were obtained by following the procedure of Example 1 using the macropolycyclic compounds (22)pyridinamide and (222$_B$) respectively:

[Eu$^{3+}$C(22)pyridinamide]

Tb$^{3+}$C(222$_B$)]

EXAMPLE 8

Preparation of the (22)bisisoquinoline macropolycyclic compound of the formula (12) and of the corresponding europium complex.

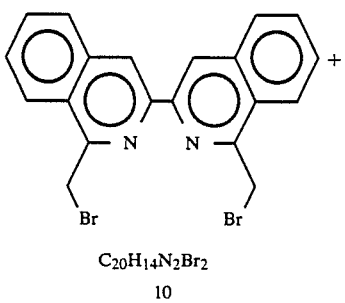

$C_{20}H_{14}N_2Br_2$
10

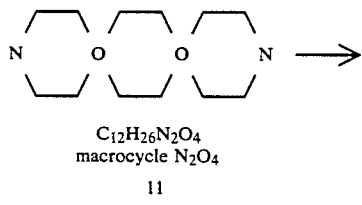

$C_{12}H_{26}N_2O_4$
macrocycle N$_2$O$_4$
11

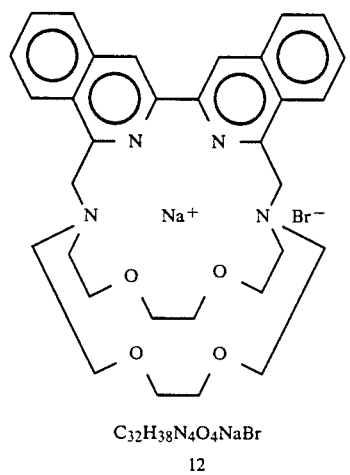

$C_{32}H_{38}N_4O_4NaBr$
12

(a) preparation of 1,1-bis(bromomethyl)-3,3' biisoquinoline of the formula 10

This compound were prepared from 1-methyl-3-hydroxyisoquinoline of formula

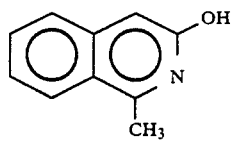

The 1-methyl-3-hydroxyisoquinoline was prepared by cyclization of N-($\pm$)-phenyl ethyl-diethoxyacetamide. 72 g of this starting compound, prepared according to the method of preparation described by H. FUKUMI et al in "HETEROCYCLES" 9(9) 1197 (1978) and purified by distillation under reduced pressure (140° C. 0.1 mmHg), were poured dropwise under stirring for one hour into 400 ml of concentrated H$_2$SO$_4$ cooled down to 10° C. The reaction mixture was cooled during the addition, so that its temperature does not exceed 10° C. The reaction mixture was then stirred for ten hours at room temperature, then poured into 600 g of ice. After filtration, the clear solution was neutralized with 20% aqueous medium under efficient cooling. The yellow precipitate was filtered off, washed with water and dried in vacuo. 41.5 g of 1-methyl-3-hydroxyisoquinoline were obtained (yield 90%). Said compound was then tosylated. A suspension of 41.5 g of 1-methyl-3-hydroxyisoquinoline was then stirred with pyridine (250 ml) under cooling in an ice-water bath. P-toluenesulfonyl chloride (70 g, 1.5 equivalent) was then gradual added over a period of 30 minutes. The yellow starting compound has then disappeared. The reaction was monitored by TLC. As soon as the reaction was complete, water (50 ml) was added, and the stirring was continued for 1 hour. It was then diluted with 700 ml of water and neutralized with solid Na$_2$CO$_3$. The resulting precipitate was filtered off, carefully washed with water and dried. 70.5 g of a non-hydroscopic product, stable in air was obtained (yield : 86%).

The resulting 1-methyl-3-p-toluenesulfonyloxyisoquinoline was then coupled according to the method of preparation described by M. Tiecco et al in SYNTHESIS 736, 1984.

In a three-necked flask equipped with a magnetic stirrer, flushed with argon, 1 of dimethylformamide (DMF), 236.3 g of triphenylphosphine and 53.5 g of NiCl$_2$, 6H$_2$O were introduced, forming a deep blue-gree solution. When the temperature of the oil bath reached 50° C., 14.64 g of zinc powder were added and the colour of the solution changed to a brown-red colour. After one hour, the solution of the starting product (70 5 g in 200 ml of DMF), namely the 1-methyl-3-p-toluenesulfonyloxyisoquinoline, was quickly added dropwise with stirring, under heating at 50° C., said temperature was maintained for additional 6 hours. After cooling down to room temperature, the reaction mixture was poured into 4 of diluted ammonia (1.51 of H$_2$O and 500 ml of 20% NH$_3$). A vigourous air stream was bubbled through the suspension to oxidize the Ni(Ph$_3$P)$_4$ (Ph=phenyl) The end of oxydation was indicated by the disappearance of the brown colour The suspension was filtered off, washed with water and placed in 400 ml of 20% HCl to change the biisoquinoline into its water-insoluble hydrochloride. The suspension was then shaked with two portions of 400 ml of ethyl ether to remove the triphenylphosphine and the acid layer was filtered off, washed with 100 ml of water and acetone to remove traces of Ph$_3$P and Ph$_3$PO. The hydrochloride was placed in a round-bottomed flask with 200 ml of 20% ammonia and stirred overnight to release the base. The white product thus obtained (26 g), namely the 1,1-dimethyl-3,3'-Biisoquinoline was filtered off, carefully washed with water and dried in vacuo (yield 81%) This product was poorly soluble in most of the solvents and sparingly soluble in CH Cl₃ and THF The 1,1-dimethyl-3,3'-biisoquinoline thus obtained was then brominated to form the 1,1'-bis (bromomethyl)-3,3'-biisoquinoline.

1.20 g of 1,1'-dimethyl-3,3'-biisoquinoline was dissolved in 500 ml of CCl₄ under reflux and N-bromosuccinimide (2.26 g, 3 equivalents) was added. After ten minutes, 10 g of 2,2'-azobis (2-methylpropionitrile) were added. The reaction was monitored by thin layer chromatography. Two other parts of initiator (10 mg each) were added over a period of one hour. After three hours, the solution was evaporated to dryness and the residue was treated with 150 ml of methanol, stirred for 30 minutes and filtered off. The resulting solid was washed with 100 ml of methanol. The filtration cake was dried in vacuo, dissolved in boiling toluene (100 ml) and quickly filtered. The product precipitated during the night in the refrigerator (1.28 g-yield:68%).

(b) Preparation of the macropolycyclic compound of the formula 12

To a mixture under stirring of 1.416 g of N₂O₄ macrocycle, and 3.39 g of Na₂CO₃ in 150 ml of CH₃CN, a suspension of 1,1'-bis (bromomethyl)-3,3'-biisoquinoline in CH₃CN (100 ml) was added over a period of 3 hours. Stirring was continued for 20 hours. After filtration and washing with CH₃CN and evaporation, a crude product was obtained and chromatographed twice, first over alumina (eluents : 3% CH₃OH in CHCl₃ then 10% CH₃OH in CHCl₃ V/V) then over silica gel (eluent 10% of CH₃OH in CHCl₃). The yield after two purifications was of 0.289 g, namely 14%. Another purification was carried out by cristallization in a mixture ethanol-ether by vapour diffusion.

(c) Preparation of the complex [Eu³⁺ C(22)biisoquinoline]

24.5 mg (1 equivalent) of anhydrous europium nitrate were dissolved in 0.5 ml of anhydrous CH₃CN. The sodium complex of (22) biisoquinoline (37.0 mg) in 0.3 ml of CH₃CN was added and the resulting mixture was treated by following the method disclosed in example 2b. The pale yellow precipitate thus obtained was diluted in 3 ml of acetonitrile and heated for 2 hours. The solution was allowed to stand at room temperature for several days. A yellow crystallized product of the formula 12 was obtained.

EXAMPLE 9:

Preparation of the (22) diphenylbipryidine macropolycyclic compound of the formula 18

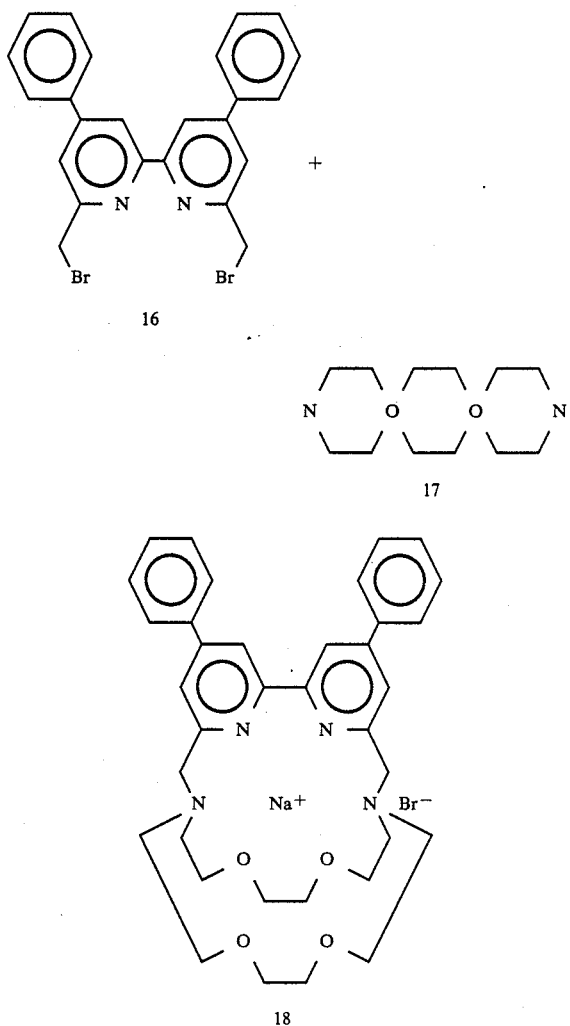

(a) Preparation of 6,6'-bis (bromomethyl)-4,4'-diphenyl-2,2'-bipridine (16)

This compound were prepared from the 4,4-diphenyl 2,2'-bipryidine available on the market, according to the following method.

6,6'-dimethyl-4,4'-diphenyl-2,2'-bipryidine

To a suspension under stirring of 4,4'-diphenyl-2,2'-bipyridine (4 g, 13 mmol) in anhydrous tetrahydrofuran (THF), cooled with an ice-bath, was added dropwise 1,5M methyllithium (3 equivalents) under nitrogen atmosphere. After this addition, the solution was stirred for additional 30 minutes under the same conditions. The dark red mixture thus obtained was then heated and stirred at 40° C. for 3 hours under nitrogen.

An excess of water was slowly added at 0° C. under nitrogen. The organic phase was separated and the aqueous phase was extracted three times with dichloromethane . Manganese dioxide was then added (20 to 40 times the weight of the starting compound) to the orange organic solution. The mixture was stirred at room temperature for 30 to 50 minutes. The reaction was followed by thin layer chromatography (Al$_2$O$_3$-eluent:toluene). Magnesium sulfate was then added to the reaction medium, which was stirred for 30 additional minutes. The filtrate was then filtered off and evaporated. The residue was chromatographed over alumina (eluent:toluene/hexane 1:1) and two products were obtained: the 6,6'-dimethyl-4,4'-diphenyl-2,2'-bipyridine (0.85 g;19%); the 6-monomethyl-4,4'-diphenyl-2,2'-bipyridine(0.45 g:10.8%)

6,6'-dimethyl-4,4'-diphenyl-2,2'-bipyridine-N,N'-dioxide

In a 250 ml flask containing an ice-cooled stirred solution of the above compound (0.28g, 0.83 mmol) in chloroform (60 ml), it was gradually added a solution of m-chloroperbenzoic acid (0.57 g 3.3 mmol) in chloroform (60 ml). Stirring was continued for 3 hours, during which the mixture was left to return to room temperature. The reaction mixture was treated with an aqueous solution of sodium bicarbonate (3.3 mmol) stirred for 30 minutes.

The organic phase was separated and evaporated in vacuo. The residue was re-dissolved in dichloromethane (CH$_2$Cl$_2$) and passed over a column of basic alumina. A second chromatography was carried out on standard alumina to completely purify the product (0.21 g; 68%).

6,6'-bis(acetoxymethyl)-4,4-diphenyl-2,2'-bipyridine 0.21 g (0.57 mmol) of the above compound was heated for one hour under reflux in acetic anhydride (1.3 ml). The solution was concentrated in vacuo and toluene was added until the formation of azeotrope of the mixture.

The resulting solid was re-dissolved in dichloromethane, washed with a 10% aqueous solution of sodium bicarbonate, dried and the solvent was evaporated. The crude product was passed over a column of silica gel and eluted with dichloromethane to give 0.126 g (yield : 49%) of the desired compound 6,6'-bis(bromomethyl)-4,4'-diphenyl-2,2'-bipyridine(16)

A solution under stirring of the above compound (0.053 g; 0.117 mmol) and of 47% hydrobromic acid (0.9 ml) was heated for 4 hours at 130° C.

The solution was then cooled in a methanol/ice-bath . 15 ml of water, 40 ml of chloroform, then gradually a saturated solution of sodium carbonate, were added thereto, until the pH of the solution became alkaline.

The organic phase was separated and the aqueous phase was extracted with chloroform (2×10 ml). All the organic fractions were combined and evaporated. The residue was chromatographed over an alumina column, with the chloroform as eluent. 40 mg (yield:69%) of the dibromide of the formula 16 were obtained.

(b) Preparation of salt [Na$^+$ C(22) diphenyl-bipyridine Br] of the formula 18

The method described in example 5b was followed by using:
21.2 mg (0.081 mmol) of N$_2$O$_4$ macrocycle of the formula 17
43 mg (0.40 mmol) of sodium carbonate
40 mg (0.081 mmol) of dibromide of the formula 16
29.8 mg (yield:53%) of the complex of the formula 18 were obtained.

EXAMPLE 10

Preparation of the diphenylbipyridine-bisbipyridine macropolycyclic complex of the formula 19

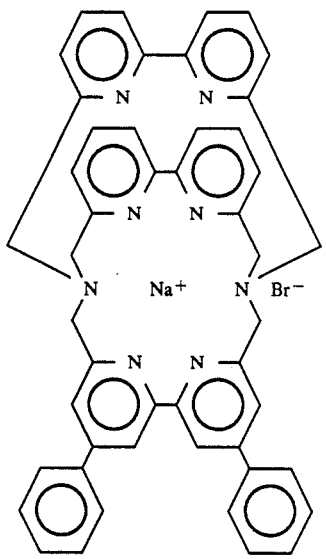

The method of the above example was repeated by using the bis-pyridine macrocycle of the formula (5) (example 5) instead of the N$_2$O$_4$ macrocycle of the formula 17. There were used:
24.7 mg (0.063 mmol) of 5 bis-pyridine macrocycle
31.1 mg (0.063 mmol) of dibromide of the formula 16
0.1 mg (0.94 mmol) of sodium carbonate
The reaction lasted for 23 hours and the compound of the formula 19 was obtained with a yield of 20%.

EXAMPLE 11

Preparation of the biisoquinoline bis-bipyridine macropolycyclic compound of the formula 20

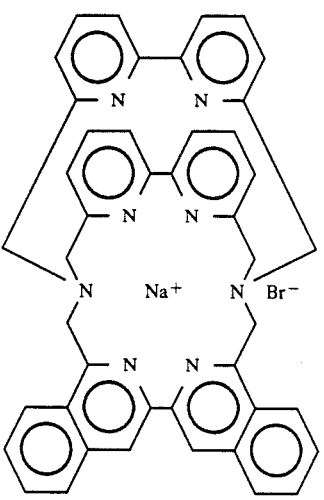

The method of the example 8 was repeated by using the bis-bipyridine macrocycle of the formula 5 instead of the N$_2$O$_4$ macrocycle of the formula 11. Equimolecular quantities of the compound of the formula 5 and of dibromide of the formula 10, were used, and the compound of the formula 20 was obtained (31.7 g ; yield : 20%)

EXAMPLE 12

Preparation of the (22) bipyridine macropolycyclic compound

Following the method of example 5 and using the N₂O₄ macrocycle of the formula 11 instead of bisbipyridine of the formula 5 and the macropolycyclic compound of the formula 21 was obtained with a yield of 12%.

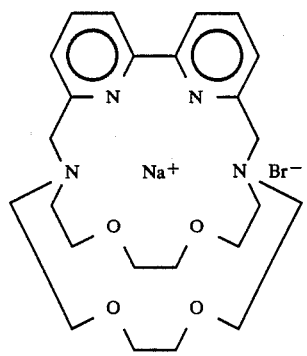

21

EXAMPLE 12

Also using the method of operation of Example 1 with the macropolycyclic compounds obtained according to examples 9 to 11, the following macrocyclic complexes were respectively obtained:

[Eu³⁺ C(22) bipyridine]

[Eu³⁺ C (bpy.biisoq.)]

[Eu³⁺ C (22) diph.bpy]

[Tb³⁺ (22) bipyridine]

Likewise, by operating according to the method of example 5, the complex [Eu³⁺ C(macropolycycle tris-phenanthroline)] was prepared by using the 6,6'-bis-bromomethyl-phenanthroline and the diamine bis (phenanthrolinediyl) macrocycle. The corresponding macropolycyclic compound had the following characteristics:

| microanalysis: $C_{42}H_{38}N_8$, NaBr, H₂O (767.6) | | | |
|---|---|---|---|
| calculated: | C 65.71 | H 4.17 | N 14.6 |
| found: | C 65.23 | H 4.26 | N 13.1 |
| RMN 1$_H$: solvent CDCl₃ | | | |
| 4.03 4.45 (very broad; AB, 12H, CH₂) | | | |
| 7.66 (d, J = 8.1; 6H; H—C(3); H—C(8)) | | | |
| 7.78 (s, 6H, H—C(5); H—C(6)) | | | |
| 8.27 (d, J = 8.1, 6H; H—C(4); H—C(7)) | | | | fluorescent characteristics of the cryptates of the invention (a) excitation peaks for a given emission wavelength For each complex was determined, for a given emission wavelength, characteristic of the rare earth ion of the complex, the excitation wavelengths the recorded excitation peaks do not correspond to those of the rare earth ion alone In addition, it has been noted that by exciting the complex at the wavelength corresponding to the excitation peak determined above, the maximum of fluorescence was characteristic of the rare earth ion.

The above determinations were made with spectrometer PERKIN-ELMER LS 5 in the operating conditions indicated in table I hereunder.

(b) Measurement of the life-time $\tau$ of europium and terbium cryptates.

On a spectrometer LS5, the emission spectrum of the peak situated between 610 and 620 nm for europium, and between 540 and 550 for terbium, was recorded, the solution being excited in one of the adsorption peaks. It was operated in phosphorescence method, the value of the slit being fixed to 1 ms=tg.

Recordings were made for several values of td (time limit) namely 0.1 ; 0.2; 0.3 ; 0.4 and 0.5ms.

The intensity of the peak It was measured and $\tau$ was determined by the formula:

$$I_t = I_o e^{-\frac{t}{\tau}}$$

$$\tau = \frac{0.434t}{\log I_o - \log I_t}$$

by tracing the curve log $I_t$.

$I_o$ may be determined and $\tau$ may be calculated as a function of td. The obtained results are indicated in table II hereunder.

TABLE I

EXCITATION AND EMISSION CHARACTERISTICS OF THE COMPLEXES OF THE INVENTION
(Perkin-Elmer LS 5)

| Complex | Concentration (solvent) | Width of the slits | Expansion factor | EXCITATION given λ emission | EXCITATION recorded λ excitation | EMISSION given λ excitation | EMISSION fluorescence maximum observed at: |
|---|---|---|---|---|---|---|---|
| [Eu³⁺C(22)phen] | 3.7 · 10⁻⁶ mol/l (water) | 2.5/20 nm | 10 | 615 nm | 290 nm(peak) 312 nm (shoulder) 330 nm (shoulder) | 290 nm | 615 nm(peak) 593 nm (second peak) |
| [Eu³⁺C(22)phenamide] | 2.5 · 10⁻⁴ mol/l (water) | 2.5/10 nm | 3 | 613 nm | 290 nm(peak) 323 nm(peak) 333 nm (shoulder) 345 nm (shoulder) | 290 nm | 613 nm 590 nm |
| [Eu³⁺C(tris-bipyridine macrocycle)] | 7 · 10⁻⁷ mol/l (0.1 M phosphate buffer, | 2.5/10 nm | 15 | 617 nm | maximum at 300 nm | 300 nm | maximum at 617 nm |

TABLE I-continued
EXCITATION AND EMISSION CHARACTERISTICS OF THE COMPLEXES OF THE INVENTION
(Perkin-Elmer LS 5)

| Complex | Concentration (solvent) | Width of the slits | Expansion factor | EXCITATION given λ emission | EXCITATION recorded λ excitation | EMISSION given λ excitation | EMISSION fluorescence maximum observed at: |
|---|---|---|---|---|---|---|---|
| [Eu$^{3+}$C(phenanthroline-bis-bipyridine)] | 2.8 · 10$^{-5}$ mol/l pH 7.5) (water) | 2.5/10 nm | 2 | | | 280 nm | 590 nm 613 nm |
| [Eu$^{3+}$C(22)bipyridine] | 10$^{-5}$ M (water) | 2.5/10 nm | 10 | 617 nm | 237 nm(peak) 303 nm(peak) | 310 nm | 617 nm 592 nm |
| [Eu$^{3+}$C(22)biisoquinoline] | 10$^{-5}$ M Tris buffer 0,01 M pH | 2.5/10 nm | 0.5 | 617 | 355 nm(peak) 325 nm(peak) | 325 nm | 617 nm |
| [Eu$^{3+}$C(22)biphenylbipyridine] | 10$^{-5}$ M H$_2$O | 2.5/10 nm | 5 | 617 nm | 254 (peak) 323 (peak) | 320 nm | 617 nm 592 nm |
| [Eu$^{3+}$C(bis-bipyridine biisoquinoline)] | 0.06 mg/ 2.4 ml of water | 2.5/10 nm | 20 | 617 nm | 310 (peak) | 310 nm | 617 nm 592 nm |
| [Eu$^{3+}$C(22) anthracene] | 0.2 mg in 3 ml of water | 2.5/10 nm | 0.2 | 613 nm | 287 nm(peak) 317 nm(shoulder) | 287 nm | 590 nm(peak) 613 nm(peak) |
| [Eu$^{3+}$C(22)bipyridine amide]* | 2 · 10$^{-4}$ mol/l (DMSO) | 2.5/5 nm | 40 | — | — | 290 nm | 613 nm 590 nm |
| [Tb$^{3+}$C 222$_B$]** | 10$^{-3}$ mol/l (DMSO) | 2.5/20 nm | 15 | 541 nm | 290 nm(shoulder) 333 nm(peak) | 290 nm | 541 nm 485 nm |
| [Eu$^{3+}$C(tris-phenanthroline)] | 0.3 mg/3 ml of Tris buffer | 2.5/10 nm | 5 | 617 nm | 272 (peak) | 270 nm | 617 nm 593 nm |
| [Tb$^{3+}$C(22)bipyridine] | 0.1 mg/2.4 ml H$_2$O | 2.5/10 nm | 1 | 617 nm | 240 (peak) 305 (peak) 314 (shoulder) | 320 nm | 545 nm 492 nm 586 nm |

*Measurement made in the phosphorescence mode; delay td = 0.1 millisecond tg = 2 milliseconds
**Measurement made in the phosphorescence mode; delay td = 0.2 millisecond tg = 5 milliseconds

TABLE II

| Macropolycyclic complex | λexcitation nm | medium | concentration | τms |
|---|---|---|---|---|
| [Eu$^{3+}$C(22)phen] | 280 | H$_2$O | 3.7 · 10$^{-4}$ M | 0.27 |
| [Eu$^{+3}$C(22) phen amide] | 280 | H$_2$O | 2.5 · 10$^{-6}$ M | 0.21 |
| [Eu$^{3+}$C(22)bipyridine] | 310 | H$_2$O | 1.2 · 10$^{-5}$ M | 0.41 |
| [E$^{+3}$C(22)biisoquinoline] | 325 | tris 0 01 M pH 7 | 10$^{-5}$ M | 0.135 |
| [Eu$^{3+}$C(22)biphenylbipyridine] | 320 | H$_2$O | 10$^{-5}$ M | 0.32 |
| [Eu$^{3+}$(tris-bipyridine)] | 300 | Phosphate buffer 0.01 M pH 7.4 | 2 · 10$^{-7}$ M | 0.43 |
| [Eu$^{3+}$(bis-bipyridine-biisoquinoline] | 311 | H$_2$O | 10$^{-5}$ M | 0.25 |
| [Eu$^{3+}$C(tris-phenanthroline)] | 272 | tris 0.01 M pH 7 | 10$^{-4}$ M | 0.32 |
| [Tb$^{3+}$C(22)bipyridine] | 318 | tris 0.01 M pH 7 | 4 · 10$^{-5}$ M | 0.72 |

We claim:

1. A macropolycyclic compound corresponding to the formula:

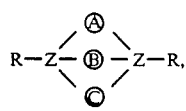

in which Z is a trivalent or tetravalent atom; R is nothing or represents hydrogen, the hydroxyl group, an amino group or a hydrocarbon radical; and the divalent radicals A, B and C independently of one another are selected from the group consisting of hydrocarbon chains, which hydrocarbon chains with one or more heteroatoms and interrupted by heteromacrocycle, wherein at least one of the radicals A, B and C includes or consists essentially of a radical selected from the group consisting of

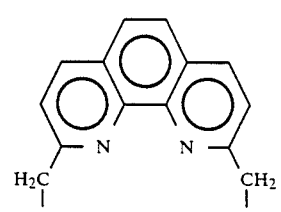

(1)

(2)
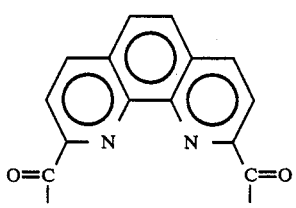

(3)
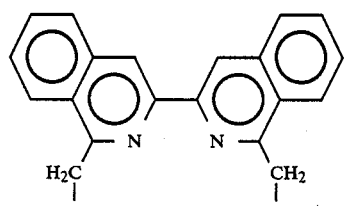

(4)
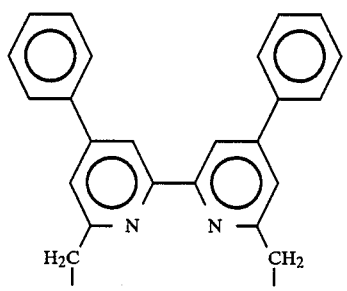

(5)
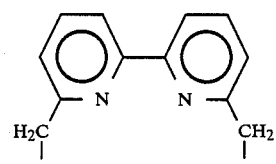

(6)
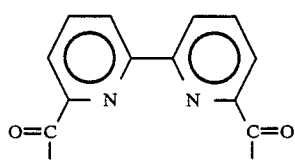

provided that when Z is N and A is radical 5 or 6, then B and C may not simultaneously be —(CH$_2$)$_2$—O—(CH$_2$)$_2$—O—(CH$_2$)$_2$—.

2. A compound of claim 1 in which at least one of the radicals A, B, and C includes or consists essentially of radical 1, 2, or 5.

3. A compound of claim 2 wherein Z is nitrogen and A and B are polyethoxylated chains.

4. A compound of claim 1 in which at least one of the radicals A, B, and C includes or consists essentially of radical 3, 4, or 6.

5. A compound of claim 4 wherein Z is nitrogen and A and B are polyethoxylated chains.

6. A compound of claim 1 wherein Z is nitrogen and A and B are polyethoxylated chains.

7. A compound of claim 1 which is a tris-biprydine macropolycycle of the formula

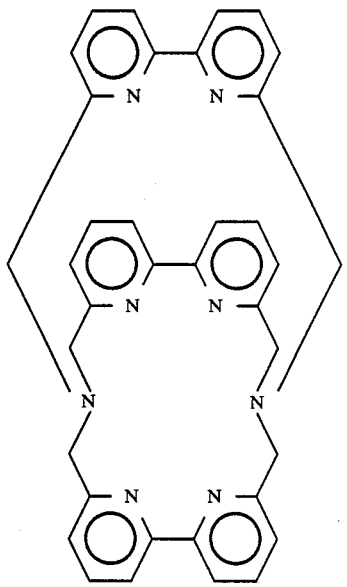

or a phenantrholine-bis-bispryidine macropolycycle of the formula

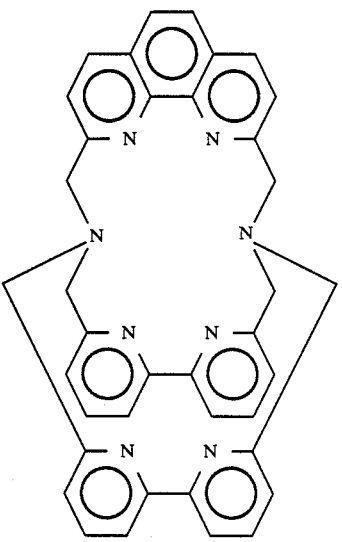

8. A compound of claim 1 which is a tris-phenanthroline macropolycycle.

9. A compound of claim 1 which is a bis-bipyridine bi-isoquinoline macropolycyle of the formula or a bis-bipyridine diphenylbipyridine macropolycycle of the formula
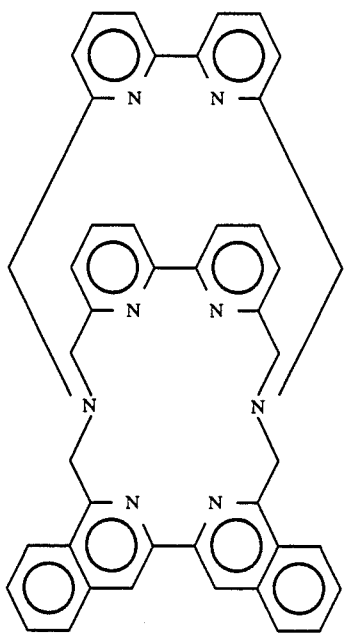
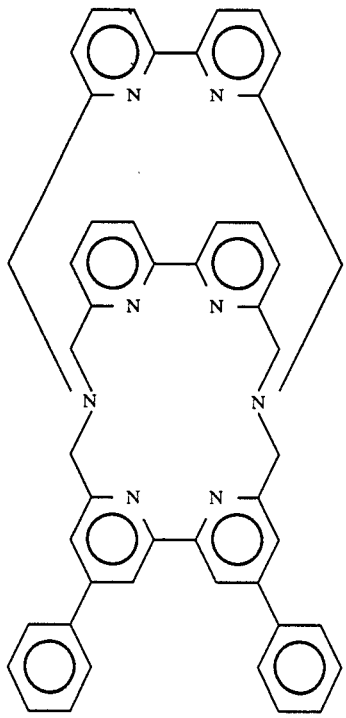
10. A macropolycyclic compound of the formula
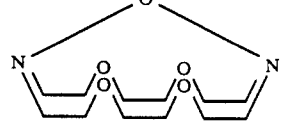
in which A is selected from the group consisting of
(1)
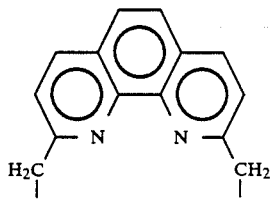
(2)
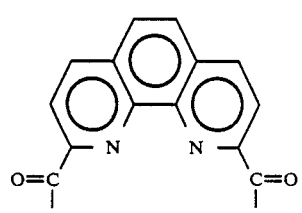
(3)
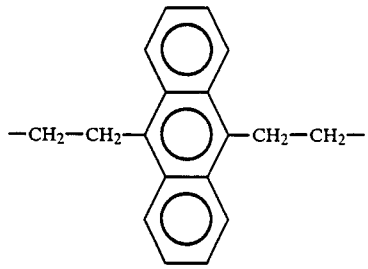
(4)
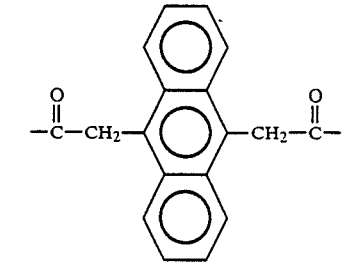
(5)
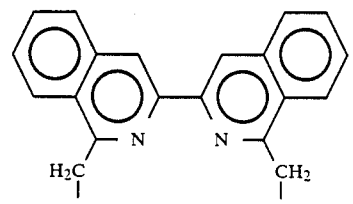
(6)
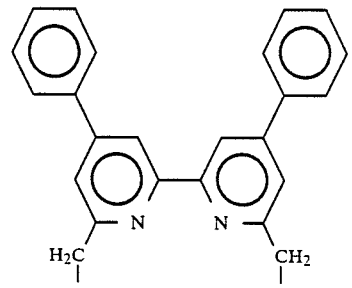
* * * * *

UNITED STATES PATENT AND TRADEMARK OFFICE
CERTIFICATE OF CORRECTION

PATENT NO. : 4,927,923
DATED : May 22, 1990
INVENTOR(S) : Gerard Mathis and Jean-Marie Lehn It is certified that error appears in the above-identified patent and that said Letters Patent is hereby corrected as shown below:

Claim 10, first compound at top of column 40 which is

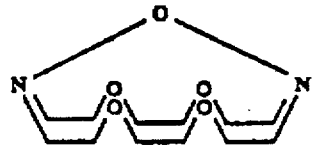

should be replaced with

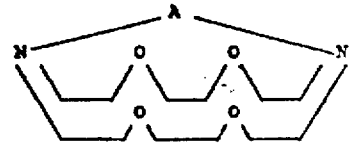

Signed and Sealed this

Fourth Day of June, 1991

*Attest:*

HARRY F. MANBECK, JR.

*Attesting Officer*    *Commissioner of Patents and Trademarks*

UNITED STATES PATENT AND TRADEMARK OFFICE
CERTIFICATE OF CORRECTION

PATENT NO. : 4,927,923            Page 1 of 3
DATED     : May 22, 1990
INVENTOR(S) : Gerard Mathis and Jean-Marie Lehn It is certified that error appears in the above-identified patent and that said Letters Patent is hereby corrected as shown below:

Column 3, line 56; delete "above." and insert --above,--

Column 7, line 44; after "2" insert -- = --

Column 8, line 30; "(22)pyridinamide" should read -- (22)pyridinamine --

Column 8, line 50; "(22)bipyridinamine" should read -- (22)bipyridinamide --

Column 10, first compound which is

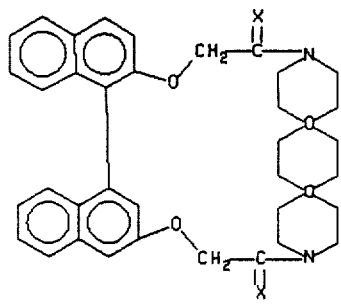

should be replaced with

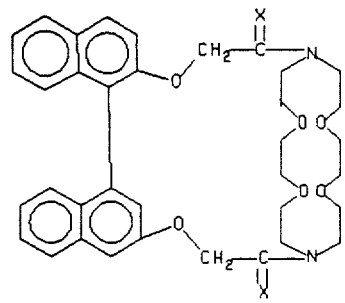

Column 14, line 7; "su" should read -- substituted --

Column 17, line 27; before "di-" insert -- ( --

Column 18, line 1 after "heating" insert -- ) --

UNITED STATES PATENT AND TRADEMARK OFFICE
CERTIFICATE OF CORRECTION

PATENT NO. : 4,927,923
DATED : May 22, 1990
INVENTOR(S) : Gerard Mathis and Jean-Marie Lehn It is certified that error appears in the above-identified patent and that said Letters Patent is hereby corrected as shown below:

Column 19, line 57; after "mmol" insert -- ) --

Column 24, line 32; "bis-hipyridine" should read -- bis-bipyridine --

Column 26, line 34; delete "wet" and replace with -- were --

Column 27, second compound which is  should be replaced with 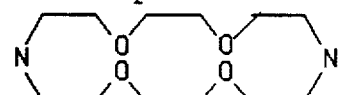

Column 28, line 30; "gradual" should read -- gradually --

Column 28, line 44; "1" should read -- 1 liter --

Column 28, line 50 and 51; "70 5" should read -- 70.5 --

Column 28, line 56; "4" should read -- 4 liter --

Column 28, line 60; after "colour" insert -- . --

Column 29, line 9; after "THF" insert -- . --

UNITED STATES PATENT AND TRADEMARK OFFICE
CERTIFICATE OF CORRECTION

PATENT NO. : 4,927,923

DATED : May 22, 1990

INVENTOR(S) : Gerard Mathis and Jean-Marie Lehn

It is certified that error appears in the above-identified patent and that said Letters Patent is hereby corrected as shown below:

Column 30, second compound which is 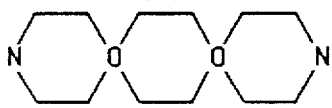   should be replaced with 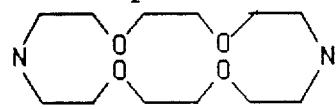

Column 34, line 18; after "wavelength" insert -- ; --

Column 34, line 20; after "alone" insert -- . --

Columns 35 and 36:
Table I-continued, last column; underneath second occurrence of "617" add -- 592 nm --

Column 35:
Claim 1, line 66; delete "which"

Column 35:
Claim 1, line 67; after "and" insert -- hydrocarbon chains --

Signed and Sealed this

Fifth Day of November, 1991

Attest:

HARRY F. MANBECK, JR.

Attesting Officer

Commissioner of Patents and Trademarks